US009416050B2

(12) United States Patent
Seidl et al.

(10) Patent No.: US 9,416,050 B2
(45) Date of Patent: Aug. 16, 2016

(54) SHELLAC-COATED PARTICLES OF ACTIVE INGREDIENTS WITH CONTROLLED RELEASE PROPERTIES AT HIGH PH-VALUES, PROCESS FOR THEIR MANUFACTURE AND USE THEREOF

(71) Applicant: Construction Research & Technology GmbH, Trostberg (DE)

(72) Inventors: Wolfgang Seidl, Palling (DE); Dawid Marczewski, Limburgerhof (DE); Sascha Raspl, Unterneukirchen (DE); Steffen Wache, Breitbrunn (DE); Michael Schinabeck, Altenmarkt (DE); Stefan Friedrich, Garching (DE)

(73) Assignee: Construction Research & Technology GmbH, Trostberg (DE)

( * ) Notice: Subject to any disclaimer, the term of this patent is extended or adjusted under 35 U.S.C. 154(b) by 0 days.

(21) Appl. No.: 14/361,849

(22) PCT Filed: Nov. 22, 2012

(86) PCT No.: PCT/EP2012/073339
§ 371 (c)(1),
(2) Date: May 30, 2014

(87) PCT Pub. No.: WO2013/087391
PCT Pub. Date: Jun. 20, 2013

(65) Prior Publication Data
US 2014/0299024 A1    Oct. 9, 2014

(30) Foreign Application Priority Data

Dec. 16, 2011   (EP) .................................... 11194032

(51) Int. Cl.
*E04C 2/02* (2006.01)
*C04B 16/04* (2006.01)
(Continued)

(52) U.S. Cl.
CPC .............. *C04B 24/34* (2013.01); *C04B 20/104* (2013.01); *C04B 20/12* (2013.01);
(Continued)

(58) Field of Classification Search
CPC ..... A61K 9/002; A61K 9/288; A61K 9/5015; A61K 9/5063; C04B 24/34; C04B 2103/0062
USPC ................... 428/403, 407; 52/309.15, 309.17
See application file for complete search history.

(56) References Cited

U.S. PATENT DOCUMENTS 3,909,444 A * 9/1975 Anderson et al. ........ 428/402.24
4,349,386 A    9/1982 Davidovits
(Continued)

FOREIGN PATENT DOCUMENTS

DE   37 04 783 A1    8/1988
GB   1 579 356       11/1980
(Continued)

OTHER PUBLICATIONS

JP 2010-180065 (2010).*
(Continued)

Primary Examiner — Holly Le
(74) Attorney, Agent, or Firm — Curatolo Sidoti Co., LPA; Joseph G. Curatolo; Salvatore A. Sidoti

(57) ABSTRACT

Suggested is a novel coated particle of active ingredients with controlled release properties at pH-values from 10 to 14, wherein the active ingredient is selected from one or more construction chemical additives for the control of inorganic binders, characterized in that the coating comprises shellac, a process for its manufacture and the use thereof as an additive for mortars, dry mortars, cement slurries and/or concretes.

17 Claims, 8 Drawing Sheets

(51) Int. Cl.
*B32B 5/16* (2006.01)
*C04B 24/34* (2006.01)
*C04B 20/12* (2006.01)
*C04B 28/02* (2006.01)
*C04B 28/14* (2006.01)
*C04B 20/10* (2006.01)
*C04B 24/26* (2006.01)
*C04B 41/00* (2006.01)
*C04B 41/45* (2006.01)
*A61K 9/28* (2006.01)
*A61K 9/50* (2006.01)

(52) U.S. Cl.
CPC .......... *C04B 24/2652* (2013.01); *C04B 28/02* (2013.01); *C04B 28/14* (2013.01); *C04B 41/0027* (2013.01); *C04B 41/0045* (2013.01); *C04B 41/0054* (2013.01); *C04B 41/0072* (2013.01); *C04B 41/4535* (2013.01); *A61K 9/288* (2013.01); *A61K 9/5063* (2013.01); *Y10T 428/2991* (2015.01); *Y10T 428/2998* (2015.01)

(56) References Cited

U.S. PATENT DOCUMENTS

| | | | |
|---|---|---|---|
| 4,472,199 A | | 9/1984 | Davidovits |
| 4,509,985 A | | 4/1985 | Davidovits et al. |
| 5,472,498 A | * | 12/1995 | Stephenson ......... C04B 20/1029 106/218 |
| 5,709,945 A | * | 1/1998 | Lee ..................... C09K 5/06 165/104.17 |
| 6,620,431 B1 | | 9/2003 | Signorino |
| 6,787,234 B2 | * | 9/2004 | Tijsma et al. ................ 428/403 |
| 6,840,318 B2 | | 1/2005 | Lee et al. |
| 7,429,392 B2 | | 9/2008 | Baum et al. |
| 7,896,068 B2 | | 3/2011 | Lee |
| 8,047,282 B2 | | 11/2011 | Lewis et al. |
| 8,460,459 B2 | | 6/2013 | Ellenrieder et al. |
| 2003/0234103 A1 | | 12/2003 | Lee et al. |
| 2004/0081827 A1 | * | 4/2004 | Datta et al. .................... 428/384 |
| 2004/0234603 A1 | | 11/2004 | Baum et al. |
| 2008/0305137 A1 | | 12/2008 | Baum et al. |
| 2011/0002986 A1 | * | 1/2011 | Durig .................. A61K 9/4891 424/463 |
| 2014/0299024 A1 | | 10/2014 | Seidl et al. |
| 2016/0122245 A1 | * | 5/2016 | Seidl ....................... C04B 20/12 106/657 |

FOREIGN PATENT DOCUMENTS

| | | |
|---|---|---|
| JP | 2002-284555 A | 10/2002 |
| JP | 2010180065 A | 8/2010 |
| RU | 2307145 C1 | 9/2007 |
| WO | WO 85/03699 | 8/1985 |
| WO | WO 85/05351 | 12/1985 |
| WO | WO 2004/000953 A1 | 12/2003 |
| WO | WO 2014/198505 A1 | 12/2014 |

OTHER PUBLICATIONS

Yassin Farag, Thesis, Characterization of different shellac types and Development of Shellac-coated Dosage Forms, 2010.*
PCT/EP2012/07339—International Search Report, Jan. 28, 2013.
PCT/EP2012/07339—International Written Opinion, Jan. 28, 2013.
PCT/EP2012/07339—International Preliminary Report on Patentability, Jun. 17, 2014.
Bilancetti, et al., "Particle coating using dry powder technology", PARTEC 2007 Conference, Mar. 27, 2007, pp. 5-8, Germany.
Farag, et al., "Physiochemical properties of various shellac types", Dissolution Technologies, May 2009, pp. 33-39, Germany.
Cheung, J., et al., "Impact of Admixtures on the Hydration Kinetics of Portland Cement", Cement and Concrete Research, Dec. 2011, pp. 1289-1309, vol. 41, Issue 12. Abstract only.

* cited by examiner

Shellac-Coated Particles of Active Ingredients with Controlled Release Properties at High pH-Values, Process for their Manufacture and Use thereof
Fig. 1: Schematic diagram of workability and setting time of a state of the art accelerated mortar and by controlled release acceleration
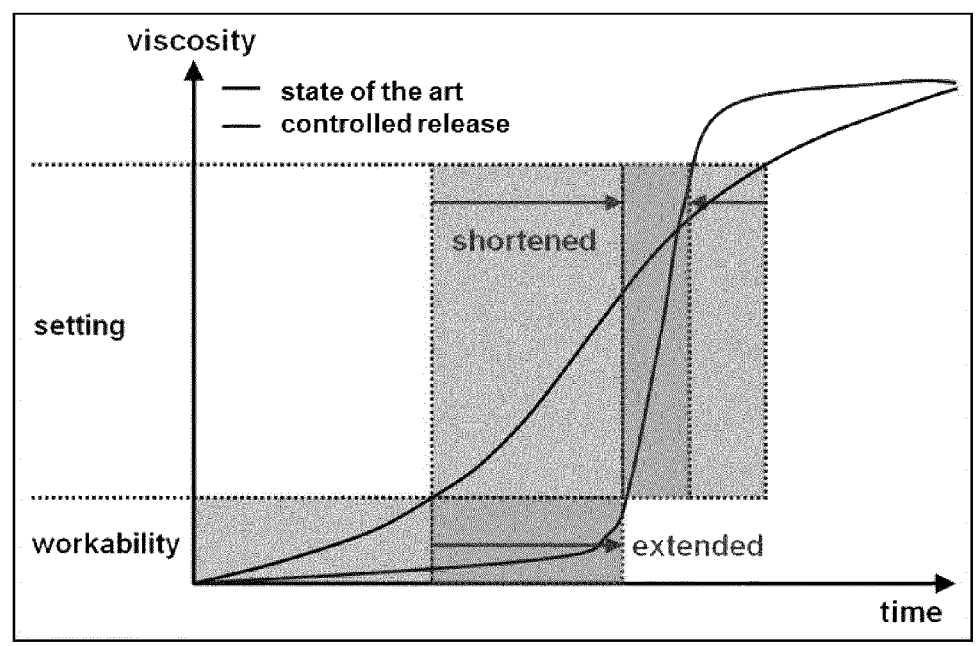

Fig. 2: Release characteristics in relation to particle geometry
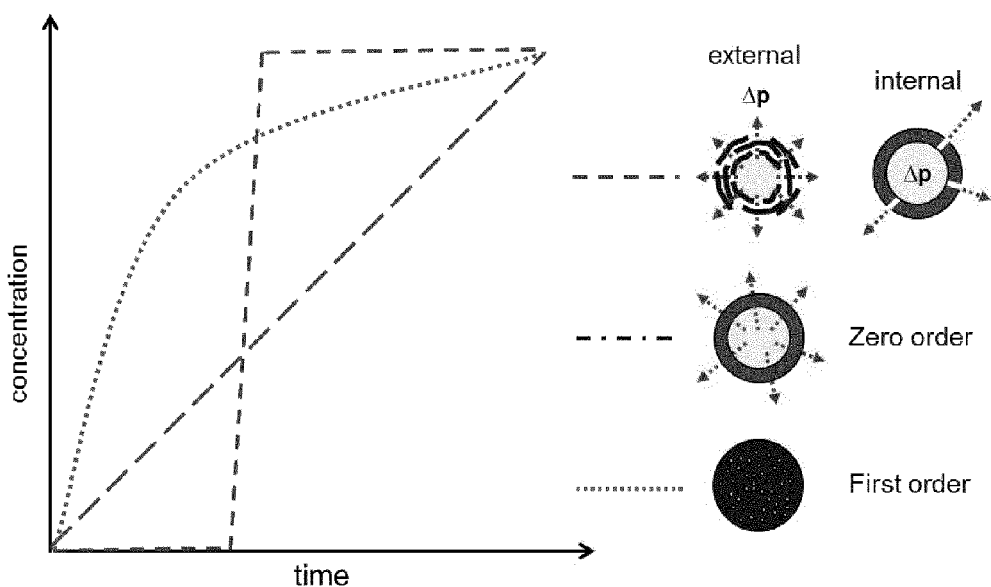

Fig. 3: Essential features for a substrate
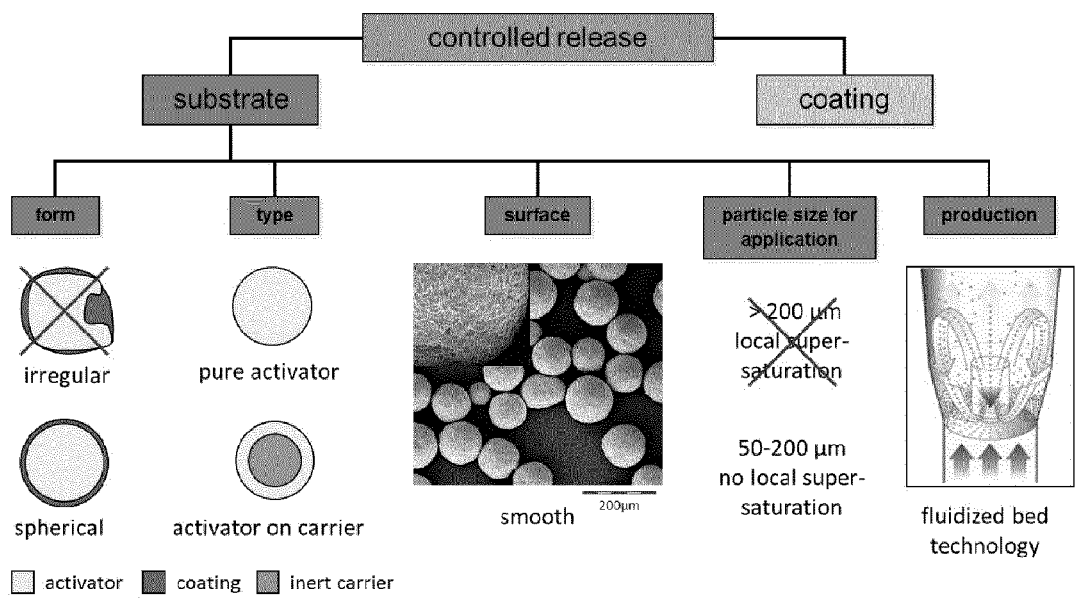
Fig. 4: Test of controlled release particles with different particle sizes and particle types
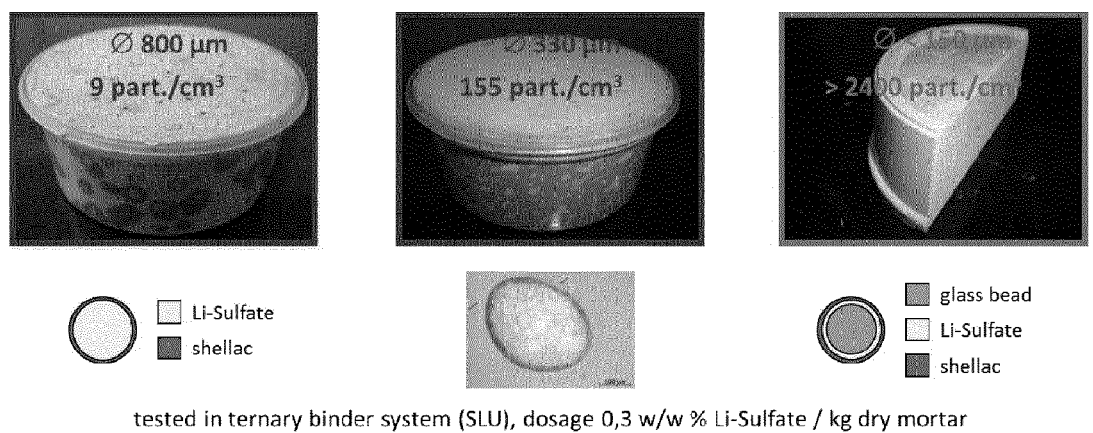
tested in ternary binder system (SLU), dosage 0,3 w/w % Li-Sulfate / kg dry mortar Fig. 5: Essential features for controlled release coating
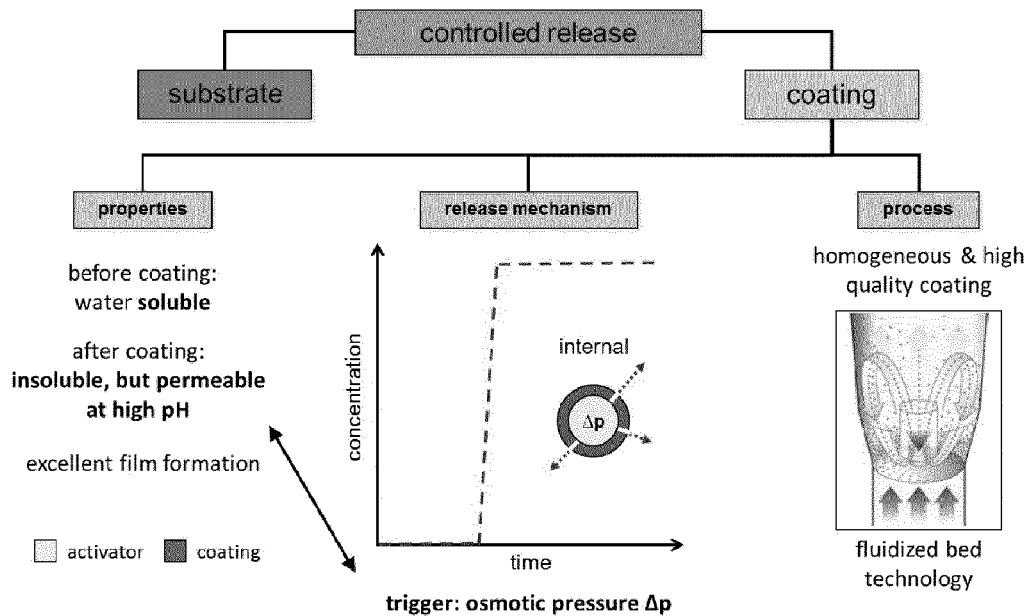
Fig. 6: Effect of coating solubility on release
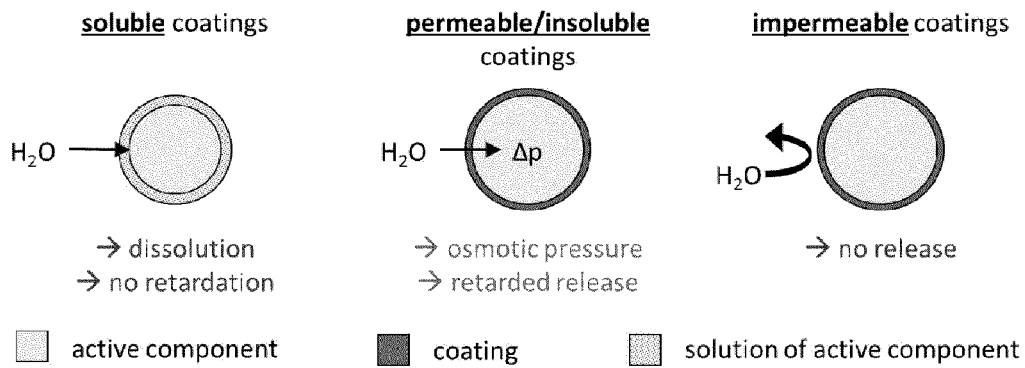

Fig. 7: Effect of coating rigidity on release mechanism
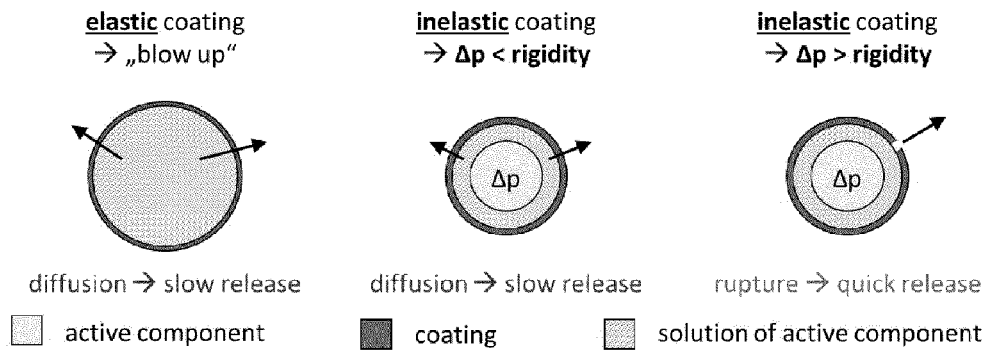
Fig. 8: Release characteristics of different coatings
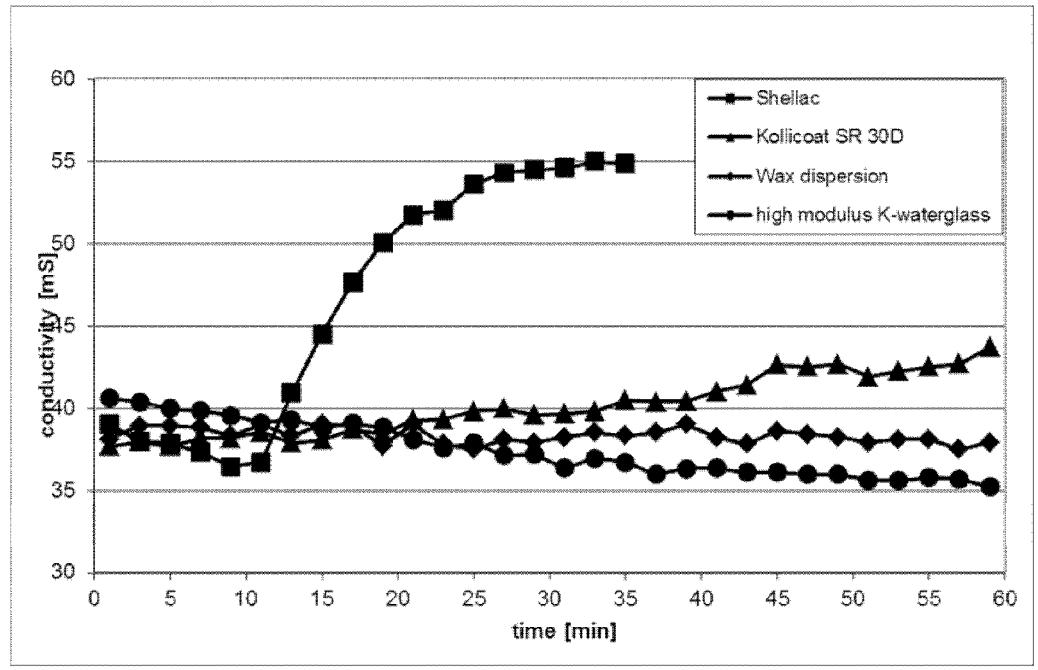

Fig. 9: General Chemical structure of shellac
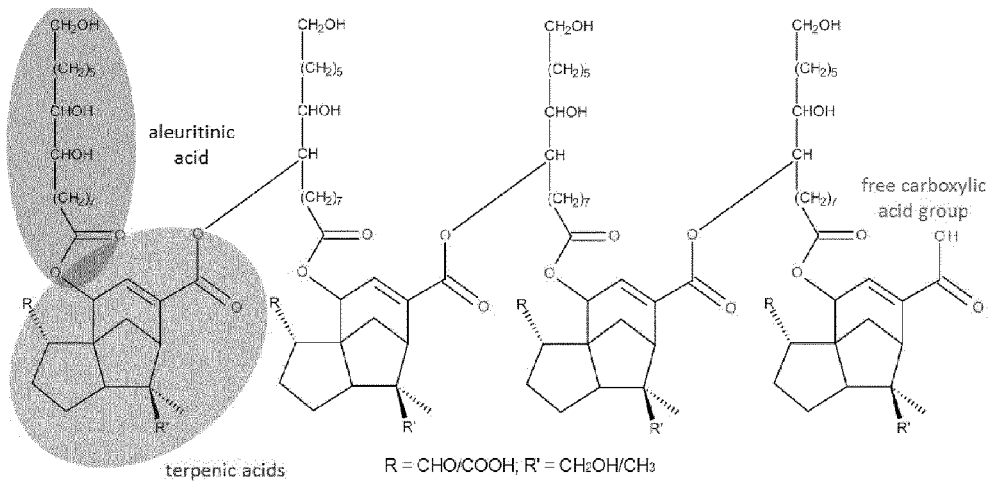
Fig. 10: Ageing of shellac at room temperature
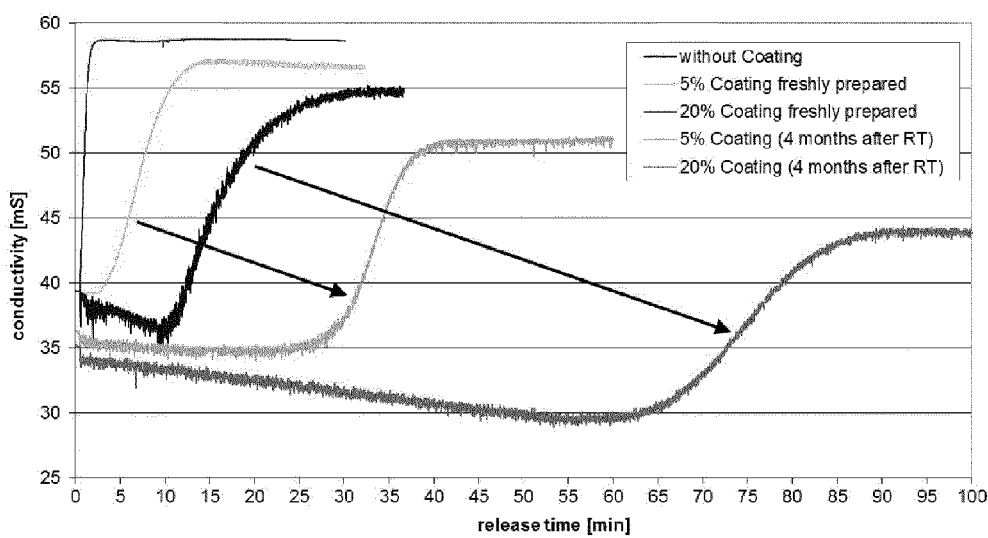

Fig.11: Heat cured Li-sulfate-monohydrate pellets with shellac coating after prolonged storage at room temperature
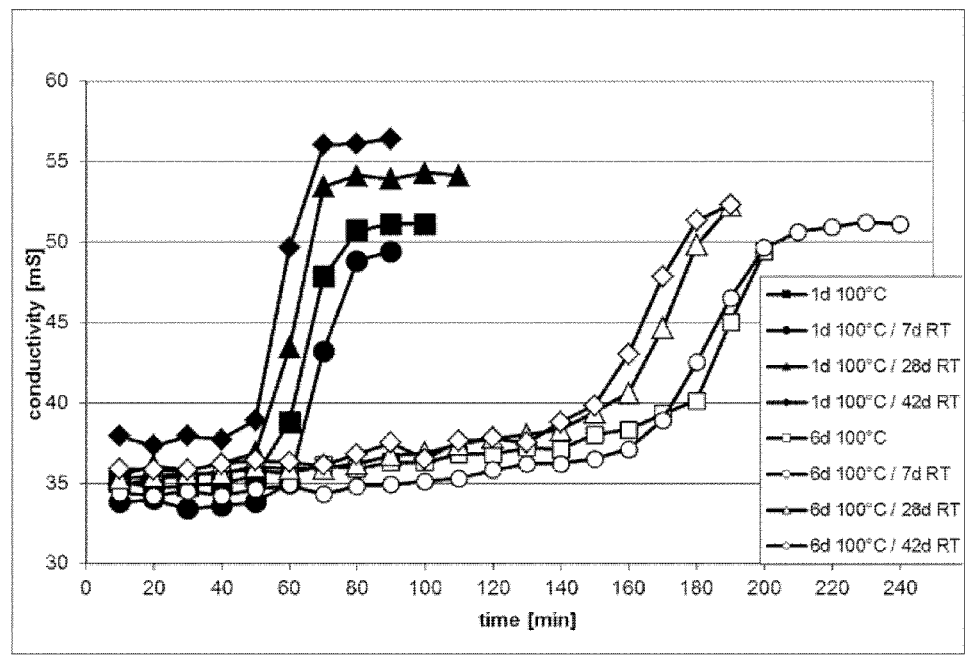
Fig.12: Release characteristic of shellac coated Li-Sulfate on glass beads after heat curing at 100 °C for different curing times
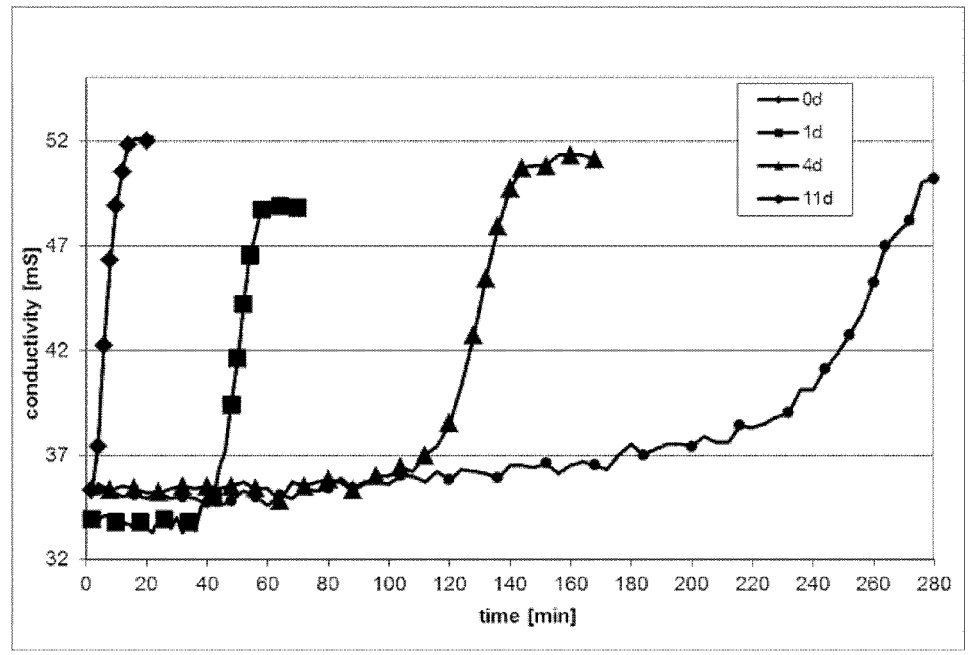

Fig.13: Release characteristic after heat curing at different temperatures and time
Release characteristic of different coatings in pore solution
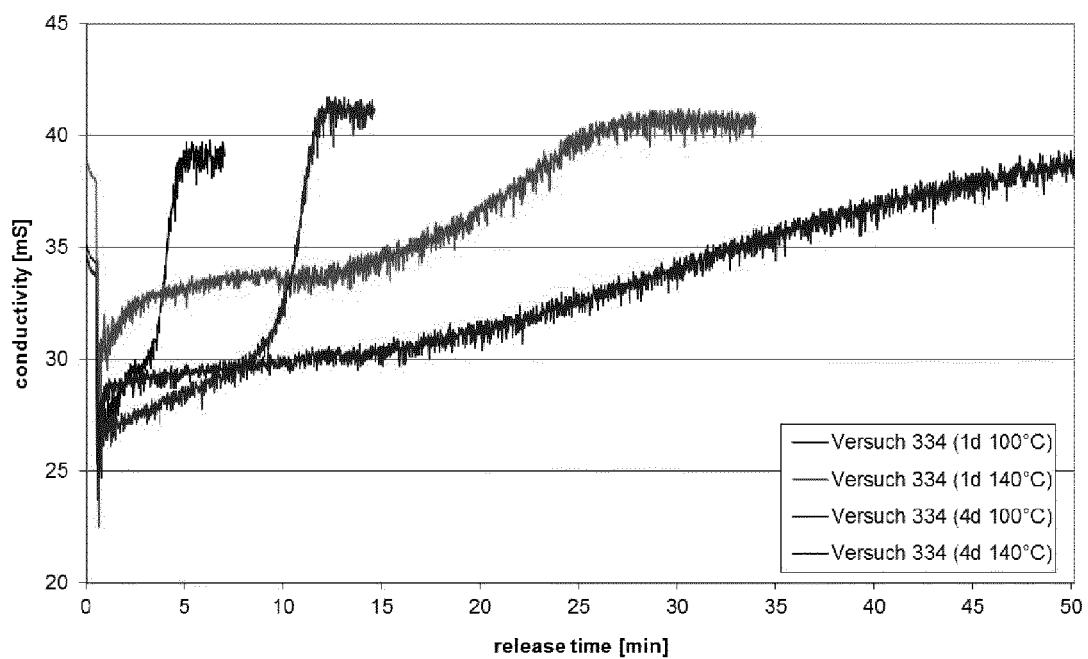

SHELLAC-COATED PARTICLES OF ACTIVE INGREDIENTS WITH CONTROLLED RELEASE PROPERTIES AT HIGH PH-VALUES, PROCESS FOR THEIR MANUFACTURE AND USE THEREOF

CROSS REFERENCE TO RELATED APPLICATIONS

This application is a national stage application of International Application No. PCT/EP2012/073339, filed 22 Nov. 2012, which claims priority from European Patent Application No. 11194032.6, filed 16 Dec. 2011, from which applications priority is claimed, and which are incorporated herein by reference.

Introduction and Technical Problem

Workability is besides material properties one of the important features of cementitious systems. On construction site, a long workability and quick setting/hardening is frequently desired, to give the craftsmen on one side plenty of time for application and on the other side do not hamper the construction progress by delayed setting/hardening. The desired mortar characteristic is usually achieved by addition of accelerators in a certain dosage. This works reasonably well, as long as the accelerator is not so potent to initiate a so called "flash-setting", as it is for example the case with shotcrete. An accelerator that causes flash setting can obviously not be used in mortars because workability time would be too short.

The problem is that workability and setting time are directly linked to each other. If for example a fast setting is required for an application, either a higher dosage of accelerator or a more potent accelerator is used, but by doing so the workability time will also be lowered. Vice versa, if a long workability is desired, the setting will be quite slow, slowing down the overall work progress (see FIG. 1). It would therefore be highly beneficial, if workability and setting time could be uncoupled from each other. Then long workability and short setting times could be achieved in one mortar (FIG. 1). If these times are furthermore adjustable as intended, this would be a very powerful tool for cementitious formulations.

Fast setting can either be achieved by high accelerator dosage or by using a highly potent accelerator. Both will shorten workability time, unless the accelerator is released only after some time. The challenge is to develop an accelerator with a controlled release characteristic. Release time should be in a range from 2 min-8 h, the release itself should be very quick so that setting can occur in short time and highly potent accelerators should be useable, to guarantee a fast setting upon release.

To develop the desired particles with controlled release characteristics the inventors of the present invention undertook extensive research and came up with the following results.

BRIEF DESCRIPTION OF THE DRAWINGS

FIG. 1 is a schematic diagram of workability and setting time of a state of the art accelerated mortar and by controlled release acceleration.

FIG. 2 is a graphical illustration of release characteristics in relation to particle geometry.

FIG. 3 is a chart illustrating features for a substrate.

FIG. 4 is an annotated representation of a test of controlled release particles.

FIG. 5 is a chart illustrating features for controlled release coating.

FIG. 6 is an illustration of the effect of coating solubility on release.

FIG. 7 is an illustration of the effect of coating rigidity on release mechanism.

FIG. 8 is a graphical illustration of release characteristics of different coatings.

FIG. 9 is an illustration of a general chemical structure of shellac.

FIG. 10 is a graphical illustration of release characteristics indicating the ageing of shellac at room temperature.

FIG. 11 is a graphical illustration of release characteristics of heat cured Li-sulfate-monohydrate pellets with shellac coating after prolonged storage at room temperature FIG. 12 is a graphical illustration of release characteristic of shellac coated Li-Sulfate on glass beads after heat curing at 100° C. for different curing times.

FIG. 13 is a graphical illustration of release characteristics after heat curing at different temperatures and time.

CONTROLLED RELEASE

Theoretic Release Mechanisms in Relation to Particle Geometry

In principle three different types of release characteristics can be distinguished. Each release type is directly linked with a specific particle geometry and coating functionality (see FIG. 2):
1. first order release=dissolution of a matrix particle
2. zero order release=diffusion
3. quick release due to internal or external trigger A matrix particle without additional coating begins to dissolve right after its activation. In the beginning, the release rate is high and it steadily decreases with time until the whole particle is dissolved. Similar to a matrix particle, a diffusion-controlled, zero order release starts right after activation, but with a steady release rate. In an ideal case the release rate does not change until the active ingredient is fully dissolved.

A totally different release characteristic is observed, when the release is internally or externally triggered after some time. No active ingredient is released until the trigger becomes active. External triggers are for example, changes in pH, temperature or application of mechanical force, such as shear stress or mechanical pressure. An internal trigger is for example osmotic pressure. The major difference between external and internal trigger is the time of activation. Functional particles releasing by external triggering do not change, as long as the trigger is not activated, but once it is, release occurs usually in a short time. In real world, this is an ideal way to release active ingredients in a lot of applications, such as in enteric pharmaceuticals (release by pH change), toner capsules in laser printers (release by temperature) or carbonless copy paper (release by pressure of a ball pen tip). In contrast, particles releasing by internal triggering need some time for activation. There is a reasonable time delay between activation and release of active compound. Of course combinations of different particle geometries combining different release characteristics in one particle are in principle possible, e.g., a matrix particle coated with a pH sensitive coating.

Referring to the demanded mortar properties (see FIG. 1) only a time delayed, but quick release of accelerator is of interest for mortar acceleration because this would allow controlling workability time. The release trigger can in principle be external or internal. Zero and first order release characteristics are not suitable because release of active component would begin right after activation, which would again shorten the workability time.

External triggering in cementitious systems is relatively complicated. The pH cannot be changed because of the development of calcium hydroxide during cement hydration. The temperature should also not be increased because cement hydration is always accelerated when temperatures increase, speeding up setting and lowering workability time. On the other side a temperature triggered release would be very interesting for retardation, because binder hydration would be slowed down due to the release of retarder when the mortar gets too warm. Application of external pressure is also no option because of the pasty consistency of fresh mortar. One possibility would be the use of ultrasonic sound on functional particles, being susceptible for such energy input. For thin mortar layers this might be a useful concept, but for larger structural parts this task is not easy to achieve.

Internal triggering is much more favorable because the addition of water to the mortar starts the activation and after some time delay, the accelerator is released. Of course in such a system, a strict control of the time delay between activation and release must be possible. A quick release can be achieved, if the coating ruptures by buildup of osmotic pressure inside the particles.

A major benefit of internally triggered functional particles is that they can be mixed homogeneously into the fresh mortar and the release starts throughout the whole matrix at the same time, resulting in a homogeneous setting.

Substrate Properties

The ideal substrate for coated particles must combine several features and depending on the intended application, a suitable way of production has to be chosen (see FIG. 3).

Particle Form

The particle form/shape has an influence on good and material-efficient coating. The ideal case is a completely spherical particle. A coating applied on such a substrate will have a homogeneous layer thickness everywhere on the particle surface and a minimum of coating material is necessary. Less coating material is favorable because coating materials are generally expensive. If the particle is less spherical, maybe formed like a potato with some knobs, it will not matter much in comparison to the ideal spherical shape. But the situation is different, if particles are highly unshaped. Then, more coating material is needed to fill up voids and empty spaces and the coating layer won't be homogeneously thick, and the effective coating thickness will be limited to the thinnest coating thickness on the whole particle. Furthermore, there is a high danger that unshaped particles and coating is abraded on edges and corners due to mechanical handling. If the coating material is cheap, as it is for example the case when natural fats can be used for coating, the larger amount of coating will not be relevant and the active ingredient can be packed into a thick coating layer, neglecting the unshaped substrate form. For some applications, like fat coated citric acid for sausage production this is sufficient, but for more sophisticated applications this could be a severe problem. Moreover, with more coating the active ingredient/coating ratio will be lowered, so less active ingredient per particle is available. If the coatings are costly a high active ingredient/coating ratio is always preferred.

Particle Type

Spherical substrates can consist either of pure active ingredient (full particle) or the active ingredient is already applied on a core (core-shell particle). Another possibility not shown in FIG. 3 would be a spherical matrix particle. The difference between a full and a core-shell particle with equal diameter is the different content of active ingredient per particle. Depending on the application, it might be necessary to choose one or the other type. A full particle is in principle preferred because it has the best possible active ingredient/coating ratio. The important point is that the substrate should not contain edges and corners.

Particle Surface

Substrate surface should be as smooth as possible, to avoid any disturbing of the later applied coating. A certain surface roughness is quite useful because the coating is then intimately linked with the substrate. Experiments have shown, that even completely smooth glass beads are suitable carriers for active ingredients such as Li-sulfate-monohydrate (see FIG. 3, picture in the middle). The particles shown have been produced by fluidized bed process.

Particle Size

An appropriate particle size of the substrate is probably an important feature in every application where functional particles are used. If particle size and application do not match, results may not be as intended. A nice example for such a mismatch can be seen in FIG. 4. There, shellac coated particles of Li-sulfate-monohydrate with different diameters have been tested in a ternary binder system consisting of ordinary Portland cement, high alumina cement and gypsum. The total dosage of active ingredient was constant in every experiment. When the particles are very large (800 μm) single blotches are formed, clearly indicating a local super saturation of accelerator. With smaller particle sizes of about 330 μm inhomogeneities are still visible, but almost every volume unit of the mortar is already reached by the accelerator. If the particle size is lowered further and with it the local concentration of active ingredient, no inhomogeneity is visible which is a clear indication that the accelerator has reached every part of the mortar matrix. It is important to mention that for the experiment on the right side in FIG. 4 coated core-shell particles (<150 μm) have been used instead of full particles.

With changing particle size also the number of particles per volume unit of mortar changes. Particle numbers per cubic centimeter increase from approximately 9 to 2400 particles when the particle diameter is lowered from 800 μm to 150 μm. In principle, when one is regarding full particles, particle number and active ingredient concentration per particle are reciprocal to each other with a cubic relationship. If the particle diameter is lowered by a factor of 2 the particle number will increase by a factor of 8. Moreover for a constant total dosage, the particle number per volume unit for coated core-shell particles is always higher than an equal sized full particle because they contain less active ingredient. Regarding the 2400 particles per cubic centimeter in the homogeneous mortar sample, the diffusion way for the accelerator is about 500 μm long. Related to the particle diameter of about 150 μm and regarding that the mortar is still a paste, containing water as a transport medium when release occurs, it is likely that the active ingredient can overcome this distance. Of course this can be already significantly different when a more potent accelerator is used or the mortar system is changed. From research results it can be concluded that a particle size of 100 to 150 μm seems to be most preferable.

Substrate Production

Depending on the intended particle size for application, several production methods might be useable. As stated above, particles with diameters of 100-200 μm will be preferred for most applications. The best production method with respect to substrate quality for such particles is the fluidized bed technology because it delivers all the demanded features mentioned above. Unfortunately, it is a relatively expensive production technology compared to particle production by pelletization or wet granulation in a high shear mixer, unless large amounts are produced, because of the necessary large technical equipment. With regard to cost efficiency, other production methods would therefore be favorable. The problem is that for example with pelletization only particles down to about 300 μm in diameter can be fabricated. As described above, these are often too large for usage.

Coatings for Controlled Release at pH>10

The demands for an appropriate coating for controlled release at pH>10 are depicted in FIG. 5 hereinbelow.

Film Formation

Firstly, a coating should exhibit a good film formation, otherwise the coating will not provide a closed, functional shell after application. Insufficient film formation can in principle be improved by addition of plasticizers. People frequently working with coatings know that the use of plasticizers not only changes film formation, but also other coating properties like solubility, permeability, E-modulus, etc. Thus whenever a plasticizer is used, the other changes in coating properties have to be taken into account. In many pharmaceutical applications the addition of plasticizers is state of the art.

Coating Solubility

Secondly, the coating should be water soluble before and insoluble, but permeable for water after the coating process.

Water soluble coatings are usually easy and convenient in use because the evaporated water in the coating process can be directly released into the environment and no additional safety measures are necessary. In contrast when working with solvent based coatings in a fluidized bed reactor, the solvent must be condensed out of the exhaust air before the air can be released into environment. Furthermore, additional safety measures for production must be taken, e.g. work under inert gas atmosphere, to prevent explosions during the coating process. It is obvious that water based coatings are preferred in daily use.

But water soluble coatings are only useable as controlled release coatings in water containing systems when two aspects are fulfilled: Firstly they are insoluble and secondly they are still permeable to water after the coating procedure. The change from soluble to insoluble is important because if a coating remains water soluble after the coating process, it would readily dissolve and hence release the active ingredient just after addition of water (see FIG. 6, left side). If the coating is insoluble and impermeable to water it would not dissolve at all, hence prohibiting any release of active ingredient (see FIG. 6, right side). This happens for example when water based wax dispersion is used as coating. Therefore, for an internally triggered release by osmotic pressure the coating must be insoluble, but permeable for the solvent after the coating (see FIG. 6, middle). Then water can penetrate through the coating into the core, there partially dissolve the core and build up osmotic pressure. If the osmotic pressure is high enough, the coating will rupture and release the salty solution into the surrounding matrix.

Hence the demanded release characteristic (FIG. 5) of functional ingredients can be achieved when the coating is switchable in solubility from soluble before to insoluble, but permeable, after the coating process.

A change in solubility can for example be achieved by change in pH when functional groups like —COOH or —$NR_2$ are protonated or deprotonated. Enteric coatings are a class of coatings that exhibit such properties. Another possibility is to irreversibly cross link the coating after the application either by additional cross linking molecules or activation of internal reactivity of the coating. But this has to be done very carefully to maintain the permeability for water.

Release Mechanism

Thirdly, to achieve a delayed, but quick, release it would be best to trigger the release internally by osmotic pressure. A precondition for internal triggering is that the coating is susceptible for internal pressure. If the coating is either too elastic or too rigid the coating would not rupture as intended (see FIG. 7, left and middle). In both cases the release characteristic would be a diffusive one (see FIG. 2). Only when the internal osmotic pressure is higher than the rigidity of the coating, the coating will rupture (see FIG. 7, right) and a quick release will be observed. Of course the coating rigidity correlates with the thickness of the coating layer. The thicker the layer, the more pressure is necessary to cause rupture.

Coating Process

Fourthly, coatings are applied best by fluidized bed technology because this technology works well for particles with diameters >100 μm and provides an excellent coating quality. Other coating technologies than fluidized bed technology can in principle be used, but most of them are only efficient for particles >500 μm. As has been described earlier such particles sizes are often too large for the intended use.

In summary a coating for controlled release at pH >10 should provide the following properties:
  good film formation
  water soluble before application
  insoluble, but water permeable at pH>10 after application
  coating rigidity must be lower than the internal osmotic pressure to provide a quick release Coating Screening To find a suitable coating with the demanded properties, a screening of many different coatings on coarse Li-sulfate-monohydrate pellets (diameter approximately 750 μm) has been carried out. Pellets have been used as substrate for the coating screening because of their smooth surface and almost round shape.

Release of active ingredient has been measured with a conductivity electrode in an open beaker in synthetic pore solution at room temperature. Synthetic pore solution is an alkaline, $Ca^{2+}$ saturated, $Na^+$, $K^+$, $SO_4^{2-}$-containing solution similar to a solution, one would obtain after mixing cement with water and then filtering off the solution, with the difference that the synthetic solution is not supersaturated. The alkaline pH value is immanent to Portland cement, due to formation of calcium hydroxide during cement hydration. For the conductivity measurements coated pellets were added to the solution 30 s after starting the measurement. The release measurement in FIG. 8 and all following release measurements are conductivity measurements in synthetic pore solution.

Shellac was the only coating that showed a desired step-like release characteristic (see FIG. 8). Other coatings like wax or high modulus water glass either did not release active ingredient at all or showed an unwanted diffusive release, such as Kollicoat SR 30 D. Most of the coatings failed the screening because of being quickly soluble in synthetic pore solution. Based on these results, shellac was chosen as coating for controlled release particles in cementitious systems.

The finding that shellac can be used at pH-values of 10-14 was most surprising as shellac has been used so far as an enteric coating in pharmaceutical applications where it dissolves already in small intestinal fluid (pH 8-8.5).

Shellac

Shellac is a natural, oligomeric ester with about eight monomeric units that is secreted by female lac bugs on trees in India and Thailand (for a chemical structure see FIG. 9). Shellac is harvested by cutting of the tree branches encrusted with it and separating it from the wood. Purification is done by dissolution in ethanol, dewaxing and cleaning it with active carbon. It contains about 50% aleuritinic acid (9,10,16-trihydroxypalmitinic acid) and different types of terpenic acids. Shellac is soluble in ethanol or, when the free carboxylic acid group is deprotonated, in mild alkaline solution at pH=8. In an acidic medium it is insoluble. In hot alkaline solution shellac can be saponified. The content of free carboxylic acid groups is defined by an acid value (mg KOH/g shellac to neutralize it) which lies typically around 70 mg KOH per 1 g shellac. Due to the large number of OH— groups, shellac exhibits excellent film forming properties.

As it is a natural product, composition and properties of shellac can vary. The globally traded amount of shellac is approximately 20,000 t per year, with a price of around 10 € per kg. Throughout the experiments referred to in this description, the shellac type SSB Aquagold® (HARKE Group, Mülheim an der Ruhr; a 25% shellac solution in water) has been used.

Ageing of Shellac

After 4 months of storage at room temperature the shellac-coated Li-sulfate samples were measured a second time and a much longer release time was observed. The shellac coating was obviously ageing (see FIG. 10). This behavior is highly problematic in dry cementitious systems because these systems have to maintain their properties at least over a time period of about 6 months. The workability and setting time adjusted by formulation should not change much during this time. A slowly ageing coating with a change in release from about 10 to more than 60 min is therefore inacceptable.

This ageing of shellac is believed to be the result of further esterification between —OH groups and free carboxylic acid groups in the oligomeric ester molecules. The more of this cross linking occurs, the lower the solubility and permeability of shellac and the higher the rigidity of a shellac coating will be.

Heat Curing of Shellac

A series of experiments was carried out to check which temperatures and which curing times are necessary to stop the ageing. It turned out that temperatures between 80 and 140° C. are sufficient, depending on the curing time. The higher the temperature the shorter is the necessary curing time to stop the ageing of shellac. At 80° C. the curing time should range from one to seven days, at 100° C. from six hours to four days, at 120° C. from one hour to two days and at 140° C. from hour to one day. However, these times are only approximate numbers and can vary with shellac type. When heat curing is prolonged above these curing times, the release time steadily increases, but the slope during release becomes less steep due to a less permeable and more rigid coating (see FIG. 12). With that, the release characteristic gradually changes from a step like quick release to a more diffusion like release of active ingredient that is not intended.

A sample of shellac coated particles was heat cured for 1 and 6 days at 100° C. and then stored at room temperature and finally measured several times during the next eight weeks (see FIG. 11). The release times did actually not change, proving that the ageing can be stopped by heat curing. The observed inaccuracies in release times are mainly a result of the conductivity measurements and the age of the pore solution.

If the curing temperature is increased to 140° C., the shellac coating loses its step like release characteristic almost completely compared to a sample heat cured at 100° C. for the same time (see FIG. 13).

Upon heat curing, the reactive carboxylic acid groups and OH-groups contained in the shellac are believed to react with one another, forming additional ester linkages. In the coating, the linkages will be established between the single oligomers forming a 3-dimensionally cross linked matrix. With this cross linking, the molecular weight is increased as well as the melting point. The increased molecular weight makes the shellac virtually insoluble, but it still remains permeable for water, which is a precondition for the buildup of internal osmotic pressure.

Heat curing should be done with aid of an anti-caking agent to prevent coated particles sticking to each other because shellac gets sticky when heated above its melting point of about 60° C. With the consecutive cross linking reaction it becomes rigid again. Fully "polymerized" shellac is only melting at temperatures above 150° C.

The invention claimed is:

1. A coated particle of active ingredients with controlled release properties at pH values from 10 to 14, characterized in that the particle having a coating comprises at least two layers in the form of a core/shell structure, wherein the active ingredient is comprised in a core area, and wherein the active ingredient is selected from one or more construction chemical additives, characterized in that the coating consists of crosslinked shellac.

2. The coated particle of claim 1, characterized in that the active ingredient is comprised in the core area and is supported on, adsorbed on, absorbed by, or mixed with a carrier.

3. The coated particle of claim 1, characterized in that the core/shell structure additionally comprises a diffusion control layer situated between the core area and the shellac coating, wherein the diffusion control layer optionally comprises methylcellulose.

4. The coated particle of claim 1, characterized in that the construction chemical additives are selected from accelerators, retarders, shrinkage control additives, water retention agents, efflorescence inhibitors, defoaming agents, air entraining agents, rheology modifiers, and mixtures thereof.

5. The coated particle of claim 1, characterized in that the construction chemical additives are selected from salts of group I-III elements, lithium salts, lithium sulfate, sodium salts, potassium salts, sodium and potassium silicates, waterglasses, magnesium salts, calcium salts, calcium chloride, calcium nitrate, calcium formate, calcium silicate, calcium silicate hydrate, ettringite, aluminum salts, sodium aluminate, aluminum sulfate, and mixtures thereof.

6. The coated particle of claim 1, characterized in that the release of the active ingredients commences within 2 minutes to 8 hours after contact with an aqueous solution of pH 10-14.

7. The coated particle of claim 6, characterized in that the release of the active ingredients commences within 2 minutes to 8 hours after contact with an aqueous solution of pH 12-13.

8. The coated particle of claim 1, having an average diameter of from 50 to 1000 μm.

9. The coated particle of claim 1, wherein the shellac coating has an average thickness of from 1 to 80 μm.

10. The coated particle of claim 1, having an average diameter of from 100 to 200 μm.

11. The coated particle of claim 1, wherein the shellac coating has an average thickness of from 1 to 30 μm.

12. Process for the manufacture of coated particles as defined in claim 1, characterized in that core particles of active ingredient are coated in a fluidized bed reactor with a solution of shellac, optionally an aqueous solution, and the coated particles are subsequently subjected to a treatment that effects crosslinking of the shellac coating.

13. The process of claim 12, characterized in that the treatment is selected from thermal treatment, treatment with microwave energy, electrical plasma, high-energy particles, and ionizing radiation, or combinations thereof.

14. The process of claim 13, characterized in that the thermal treatment is carried out at temperatures of 80 to 140° C., for 1 hour to 7 days.

15. The process of claim 14, characterized in that the thermal treatment is carried out at temperatures of 100 to 120° C.

16. A process comprising utilizing the coated particles as defined in claim 1 as an additive for mortars, dry mortars, cement slurries and/or concretes.

17. A coated particle of active ingredients with controlled release properties at pH values from 10 to 14, characterized in that the particle having a coating comprises at least two layers in the form of a core/shell structure, wherein the active ingredient is comprised in a core area, and wherein the active ingredient is selected from one or more construction chemical additives, characterized in that the coating consists essentially of crosslinked shellac and at least a disintegrant, a wax, a plasticizer, a hydrophobization agent, a polyvinylpyrrolidone, a filler, a salt, or mixtures thereof.

* * * * *